(12) United States Patent
Sandoz et al.

(10) Patent No.: US 10,908,070 B2
(45) Date of Patent: Feb. 2, 2021

(54) METROLOGY DEVICE AND ASSOCIATED METHOD

(71) Applicant: TECSAN, Sion (CH)

(72) Inventors: Jean-Luc Sandoz, Ecublens (CH); Yann Benoit, Saint-Sulpice (CH); Jean-Daniel Gasser, Bussigny (CH)

(73) Assignee: TECSAN, Sion (CH)

( * ) Notice: Subject to any disclaimer, the term of this patent is extended or adjusted under 35 U.S.C. 154(b) by 417 days.

(21) Appl. No.: 15/561,151

(22) PCT Filed: Mar. 18, 2016

(86) PCT No.: PCT/EP2016/056057
§ 371 (c)(1),
(2) Date: Sep. 25, 2017

(87) PCT Pub. No.: WO2016/150882
PCT Pub. Date: Sep. 29, 2016

(65) Prior Publication Data
US 2018/0100794 A1 Apr. 12, 2018

(30) Foreign Application Priority Data
Mar. 24, 2015 (FR) ...................................... 15 52471

(51) Int. Cl.
*G01N 19/10* (2006.01)
*G01N 27/04* (2006.01)
(Continued)

(52) U.S. Cl.
CPC ............... *G01N 19/10* (2013.01); *G01N 3/58* (2013.01); *G01N 27/041* (2013.01);
(Continued)

(58) Field of Classification Search
CPC ........ G01N 19/10; G01N 3/58; G01N 27/041; G01N 33/46; G01N 27/048; G06F 17/11
(Continued)

(56) References Cited

U.S. PATENT DOCUMENTS 2,389,030 A 11/1945 Homer
4,196,616 A * 4/1980 Argabrite ................. G01N 3/42
73/81

(Continued)

FOREIGN PATENT DOCUMENTS

NL 9101010 A 1/1993

OTHER PUBLICATIONS

Written Opinion, Translated, from parent PCT application PCT/EP2016/056057, undated, 5 pages.
(Continued)

*Primary Examiner* — Marrit Eyassu
(74) *Attorney, Agent, or Firm* — Tech Valley Patent, LLC; John Pietrangelo

(57) ABSTRACT

The invention relates to a metrology device for determining the quality of a hygroscopic material. The metrology device includes a frame, a support element, two tips that can move in translation with respect to the frame, means for measuring a penetration effort of each tip as a function of a force applied to each tip, means for measuring an electrical resistivity between the ends of the two tips, which means are able to measure an electrical resistivity of the hygroscopic material when the two tips are inserted into the hygroscopic material, and means for measuring a penetration effort of the support element as a function of a force applied to the support element in order to achieve a predetermined fixing position. The support element is adapted to penetrate into the hygroscopic material so as to fix the frame to the hygroscopic material.

20 Claims, 3 Drawing Sheets

(51) Int. Cl.
*G01N 33/46* (2006.01)
*G01N 3/58* (2006.01)
*G06F 17/11* (2006.01)

(52) U.S. Cl.
CPC ............ *G01N 27/048* (2013.01); *G01N 33/46* (2013.01); *G06F 17/11* (2013.01)

(58) Field of Classification Search
USPC ............................................................ 73/81
See application file for complete search history.

(56) References Cited

U.S. PATENT DOCUMENTS

| | | | |
|---|---|---|---|
| 4,249,414 A * | 2/1981 | Barth | G01N 3/42 73/81 |
| 4,343,179 A | 8/1982 | Astroem et al. | |
| 4,671,105 A * | 6/1987 | Kamm | G01N 3/42 73/81 |
| 5,567,871 A | 10/1996 | Sandoz | |
| 2003/0131674 A1* | 7/2003 | Foley | G01N 3/40 73/866 |
| 2014/0352458 A1* | 12/2014 | Kaufhold | G01N 33/46 73/865.8 |
| 2015/0233806 A1* | 8/2015 | More | G01N 3/42 73/85 |

OTHER PUBLICATIONS

International Search Report from parent PCT application PCT/EP2016/056057 dated Jun. 13, 2016, 4 pages.
Written Opinion from parent PCT application PCT/EP2016/056057, undated, 5 pages.
Ezer, Edward, "Measurement of wood pole strength-Polux(R) a new nondestructive inspection method," 2001.

* cited by examiner

METROLOGY DEVICE AND ASSOCIATED METHOD

CROSS-REFERENCE TO RELATED APPLICATIONS

This application is a § 371 filing of PCT application PCT/EP2016/056057 filed on Mar. 18, 2016, which claims priority from French application FR 1552471 filed on Mar. 24, 2015. The disclosures of these applications are included by reference herein in their entirety.

BACKGROUND

Technical Domain

The present invention concerns a metrology device for determining the quality of a hygroscopic material, such as wood or other similar construction materials. The present invention also concerns the associated method.

The invention relates more particularly to determining the quality of wooden poles used by electricians for the distribution and transmission of energy as well as by telecommunications organizations for cabled networks or for aerial optical fiber networks.

Prior Art

There are millions of wooden poles in service throughout the world that must be periodically checked to ensure maintenance of the lines for two primary reasons. First, the quality of the wooden poles involves the safety of people working alongside these poles, and public authorities often require the preventive maintenance of these infrastructures. Secondly, knowledge of the quality of wooden poles makes it possible to anticipate future replacements within the network.

For many years, experienced men who strike the pole with a hammer in order to listen to the resonance properties thereof have inspected wooden poles. This method, although empirical, provided results that are relatively satisfactory and in any case are better than with networks where no inspection is made.

For several decades, non-destructive technologies based on physical measurements of the wood have appeared.

The U.S. Pat. Nos. 2,389,030 and 4,343,179 describe a resistograph type technology, relating to the density of the wood, which consists in causing an element to penetrate into the wood and measuring the effort necessary for the penetration of the element. In the case of the first document, a support is attached to the pole by means of two tips that are short in length and by a strap around the pole. A manual device into the wood screws a metal bore bit, guided by the support, and the resistance to the screwing of the bit is measured. In the case of the second document, an operator holds the device against the pole and causes the linear penetration of a tip by a dynamometric system. When the tip penetrates the pole, a ruler measures the resistance to the penetration of the tip.

These two methods make it possible to obtain a densitogram upon which it is possible to observe pockets of decay or pockets of low density inside the pole.

However, these methods do not provide any direct diagnosis about the residual structural performance of the pole and therefore its level of safety. They are limited to showing that there is more or less serious biological degradation inside the pole. Furthermore, these methods do not detect poles with no decay but that could contain only relatively weak fibers and could consequently prove to be very weak in mechanical performance, thus representing a risk. Moreover, these methods are incapable of giving any estimate of the amount of time the pole could remain in service. It is a rather binary method, indicating either that the pole contains deterioration, or that it does not.

The patent FR 2 707 759 makes it possible to overcome these obstacles by proposing a method that seeks to quantify a residual value of bending performance as well as an estimated expectation of the working life of the pole. This method consists in attaching a frame to the pole by means of two strap-type support elements. Two tips are manually moved in translation in relation to the frame in order to penetrate into the pole and enable measurement both of a penetration effort of each tip in the pole and an electrical resistivity between the ends of the two tips when the two tips are inserted into the pole. The electrical resistivity between the two tips of the pole makes it possible to determine the hygroscopy of the wood deep inside the pole.

However, this method has the disadvantage of taking rather long to carry out because an operator must securely attach the two strap-type support elements before proceeding with the first measurement.

DESCRIPTION OF THE INVENTION

The present invention seeks to improve the precision of existing devices by means of a third additional measurement corresponding to the penetration effort of a support element into the pole. The step of attaching the frame by an operator thus becomes a first measurement step.

According to a first aspect, the invention concerns a metrology device for determining the quality of a hygroscopic material, such as wood or other similar construction materials, comprising:
 a frame,
 a support element suitable for attaching the frame to the hygroscopic material,
 two tips that can move in translation with respect to the frame,
 means for measuring a penetration effort of each tip as a function of a force applied to each tip in order to reach a predetermined distance,
 means of measuring an electrical resistivity between the ends of the two tips, which means are capable of measuring an electrical resistivity of the hygroscopic material when the two tips are inserted into the hygroscopic material, and
 means of measuring a penetration effort of the support element as a function of a force applied to the support element to achieve a predetermined fixing position, the support element being able to penetrate into the hygroscopic material in such a way as to fix the frame to the hygroscopic material.

The invention thus enables accuracy to be improved of measurements that are made on hygroscopic materials, particularly wooden poles. Fixing the frame to the hygroscopic material is no longer a loss of time for the operator because a first measurement can be made directly during this phase.

Unlike other devices held by strapping around the pole, the invention makes it possible to avoid cleaning the base of the pole in order to position the strapping. Moreover, some poles are positioned against a wall or along a sidewalk, preventing the strapping from being positioned at the base of the pole. A sheath can also be positioned along the pole. In that case, the tightening of the strapping could damage the sheath. The invention also makes it possible to overcome these disadvantages.

According to one embodiment, the device comprises:
at least one motorized means of moving tips and/or the support element, said movement means being controlled by a movement control, and
at least one means of regulating the control of movement.

An operator whose efforts fluctuate between two steps implements devices of the prior art mechanically. This embodiment improves the precision of measurements performed by regulating the accuracy of the movements of the tools.

According to one embodiment, the device comprises at least one independent source of energy. This embodiment allows the device to be energy-independent and portable.

According to one embodiment, the device comprises a part to guide the position of the frame in relation to the hygroscopic material, the guide part comprising two tips suitable for being inserted several millimeters into the hygroscopic material. This embodiment improves the precision of the first measurement made during the screwing of the support element, because the position of the device is guided.

According to one embodiment, the tips and/or the support element are mounted on fixing elements removable with respect to the frame. This embodiment enables the tips and/or support element to be changed easily during a maintenance operation, or adaptation of the tools to the hygroscopic material.

According to one embodiment, the device comprises:
means of storing the penetration effort values of each tip, the electrical resistivity and the penetration effort of the support element, and
processing means capable of estimating the safety status and remaining working life of the hygroscopic material as a function of the values of the penetration efforts of each tip, of the electrical resistivity and of the penetration effort of the support element.

This embodiment makes it possible for the operator to quickly deliver an estimate about the condition of the hygroscopic material.

According to one embodiment, the device comprises:
transmission means located inside the frame capable of transmitting the values for the penetration efforts of each tip, the electrical resistivity and the penetration effort of the support element, and
a field computer, remote with respect to the frame, comprising:
reception means capable of receiving the information from the transmission means located inside the frame,
means of storing parameters of the hygroscopic material, and
processing means integrated into the field computer capable of estimating the safety status and remaining working life of the hygroscopic material as a function of the values for the penetration efforts of each tip, the electrical resistivity and the penetration effort of the support element, and parameters of the hygroscopic material.

This embodiment makes it possible to centralize a plurality of measurements from a plurality of hygroscopic materials and to obtain an overall estimation of a large supply of hygroscopic materials.

According to one embodiment, the parameters of the hygroscopic material comprise the substance of the hygroscopic material, the diameter, type of chemical processing undergone by the hygroscopic material, and the aboveground length of the hygroscopic material. This embodiment improves the precision of estimates regarding the hygroscopic material health status.

According to one embodiment, the predetermined insertion distance of the tips is between 40 and 60 mm. This embodiment makes it possible to perform the measurements at the core of the hygroscopic material.

According to one embodiment, the support element is a wood screw wherein the diameter thereof is adapted to the substance and diameter of the hygroscopic material. This embodiment improves the reliability of the fixing between the frame and the hygroscopic material.

According to a second aspect, the invention concerns a metrology method for determining the quality of a hygroscopic material, such as wood or other similar construction materials, comprising the steps consisting of:
inserting two tips into the hygroscopic material up to a predetermined distance,
measuring, for each tip, a penetration effort as a function of the force applied to each tip to reach a predetermined distance,
when the two tips have reached the predetermined distance, measuring an electrical resistivity between the ends of the two tips inserted into the hygroscopic material,
estimating an internal hygrometry of the hygroscopic material as a function of the electrical resistivity,
inserting a support element into the hygroscopic material at an angle with respect to the frame that is substantially equal to the angle of penetration of the tips with respect to the frame,
measuring a penetration effort applied to the support element in order to reach a predetermined fixing position, and
estimating the safety status and remaining working life of the hygroscopic material as a function of the values of the penetration efforts of each tip, the electrical resistivity and the penetration effort of the support element.

The angle of the support element with respect to the frame being substantially equal to the angle of the tips with respect to the frame, the force exerted on the frame during insertion of the tips into the hygroscopic material has a direction opposite to the holding force of the frame by the support element. This second aspect of the invention thus makes it possible to angularly orient the device with respect to the height of the hygroscopic material while limiting the risks of pulling the device out. The invention also enables the tips to be inserted farther into the hygroscopic material without passing through the hygroscopic material.

According to one embodiment, the hygroscopic material being planted in the ground, the step consisting of inserting a support element into the hygroscopic material is performed at ground level. This embodiment makes it possible to insert the tips into the hygroscopic material beneath ground-level in an area particularly favorable for the formation of decay within the hygroscopic material.

According to one embodiment, the support element penetrates into the hygroscopic material at an angle with respect to the ground that is substantially equal to the angle of penetration of the tips with respect to the ground.

According to one embodiment, the support element and the two tips in the hygroscopic material are produced at an angle between 30 and 45 degrees with respect to the ground.

According to one embodiment, the hygroscopic material being planted in the ground, the step consisting of inserting a support element into the hygroscopic material is performed at an angle between 30 and 45 degrees with respect to the ground so that the support element penetrates beneath the ground level.

BRIEF DESCRIPTION OF THE FIGURES

The manner to implement the invention as well as the advantages deriving therefrom will be clearly seen from the following embodiment, provided by way of non-limiting example, as a function of the appended figures in which

FIG. 1: a schematic representation in lateral cross section of a device for measuring the quality of a pole;

FIG. 2: a schematic representation in horizontal cross-section of the device of FIG. 1 in a first step;

FIG. 3: a schematic representation in horizontal cross-section of the device of FIG. 1 in a second step;

FIG. 4: a schematic representation in horizontal cross-section of the device of FIG. 1 in a third step;

FIG. 5: a flowchart of the steps of a metrology method using the device of FIG. 1.

DETAILED DESCRIPTION OF THE INVENTION

Figure 1:
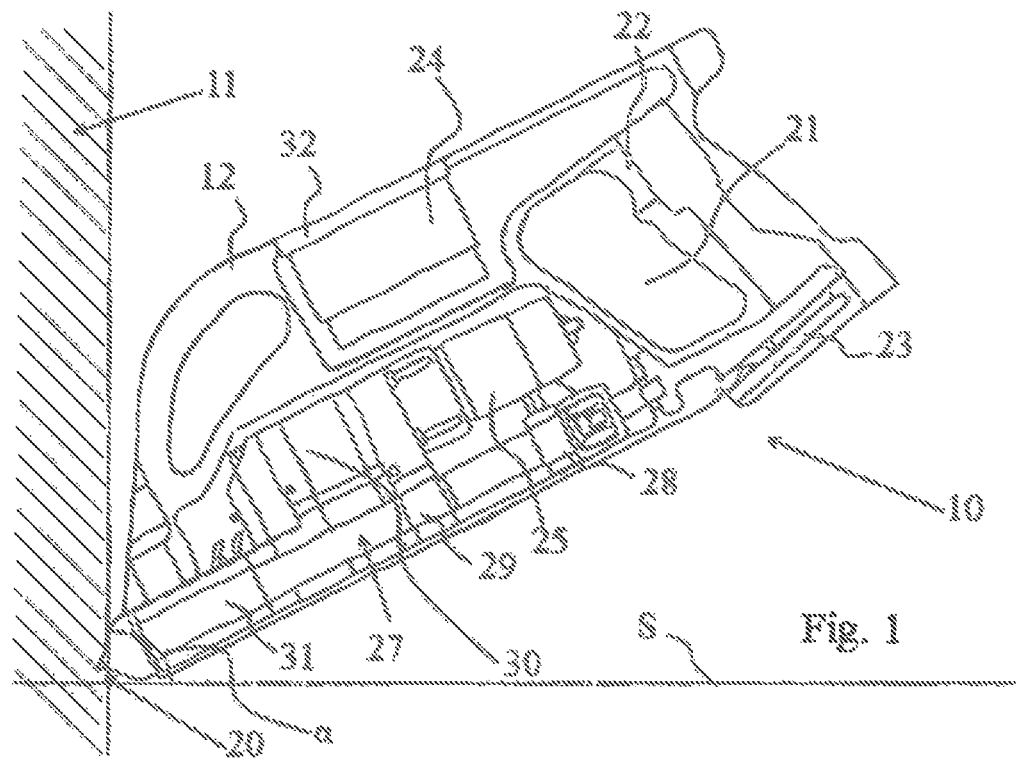
FIGS. 1 to 5 represent.

The embodiment of FIGS. 1 to 4 illustrates a device 10 for measuring the quality of a wooden pole 11. The wooden pole 11 is inserted into the ground S at an angle substantially equal to 90 degrees between the height of the pole 11 and the ground S.

The device 10 comprises a frame 12 integrating a handle 21 wherein an electrical trigger 22 is arranged. The trigger 22 is supplied by a power supply circuit 23 connected to a battery 25 and enables activation information to be transmitted to a command and control circuit 24. The command and control circuit 24 controls an actuator 27 comprising two chambers 28, 29 actuated by a servo valve 30. The battery 25 also supplies the servo valve 30 and the command and control circuit 24. The actuator 27 is associated with a coupling 31 enabling the movements of the actuator 27 to be connected either to a screw 14 or to two tips 15a, 15b. The command and control circuit 24 also controls the coupling 31.

Two sensors 17, 19, measure the movement efforts of the actuator 27. A first sensor 17 is capable of measuring the penetration efforts Ev of the screw 14 into the wooden pole 11, and a second sensor 19 is capable of measuring the penetration efforts Ep of the two tips 15a, 15b into the wooden pole 11. A third sensor 18 enables an electrical resistance Re of the wooden pole 11 to be measured between the two ends of the two tips 15a, 15b when they are inserted into the wooden pole 11. These three measurements are transmitted to the command and control circuit 24 which displays said measurements on a display 32.

Preferably, the device 10 comprises a guide part 33 comprising two tips 34a, 34b that are fixed with respect to the frame 12 and are located on either side of the device 10 at the front end 20 thereof.

Figure 2:
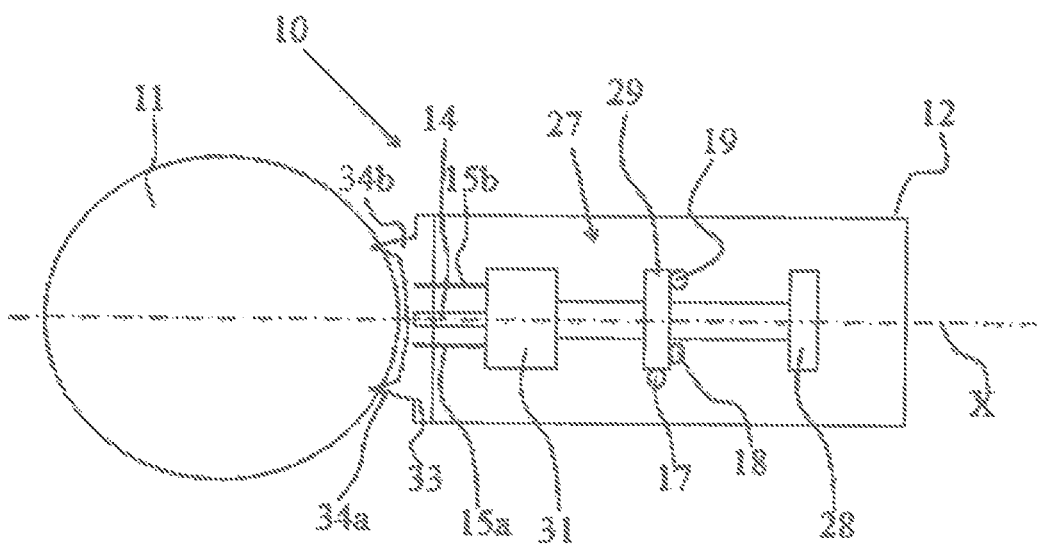
Figure 5:
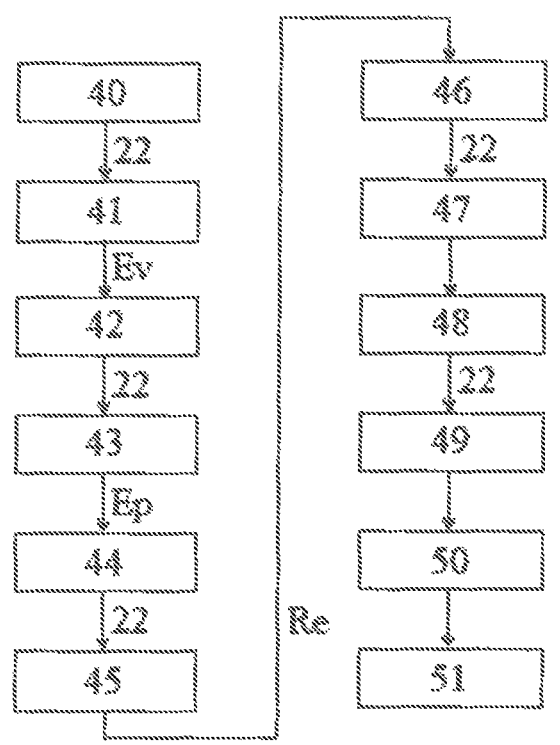

FIG. 5 illustrates the steps of a method for measuring the quality of the wooden pole 11 implemented by an operator. In a first step 40 the operator places the device 10 against the pole 11 as represented in FIGS. 1 and 2. The two tips 34a, 34b of the guide part 33 are inserted a few millimeters into the pole 11 in such a way as to center the orientation of the device 10 with respect to a line X passing substantially through the diameter of the pole 11. Moreover, the device 10 is tilted with respect to the ground S at an angle α of between 30 and 45 degrees. During this step 40, the operator estimates the position of the device 10 with respect to the pole 11 with the naked eye. As a variant, the device 10 can comprise means for improving the detection of said position (laser, ruler, etc.).

Figure 3:
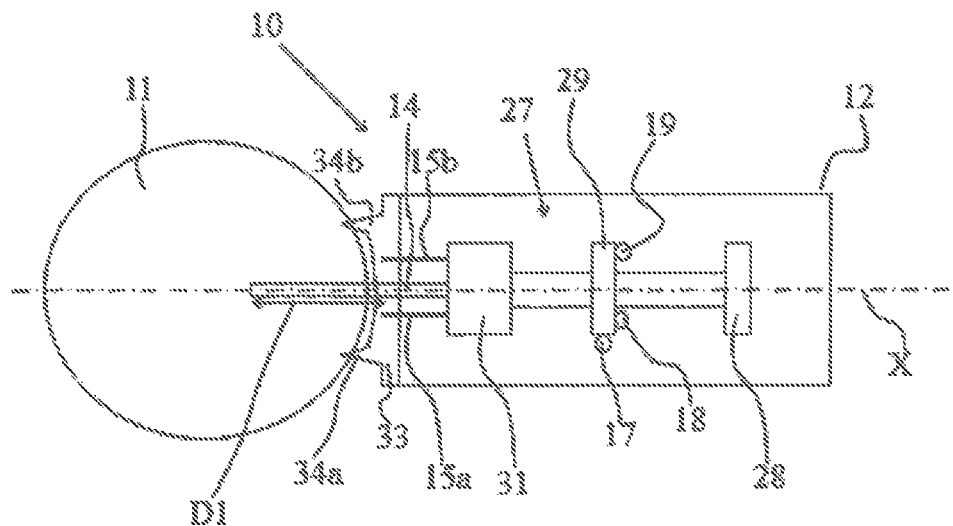

When the device 10 is correctly placed onto the pole 11, the operator actuates the trigger 22. In step 41, the circuit 24 then controls the coupling 31 in order to associate the movements of the actuator 27 with the screw 14. The circuit 24 also actuates the actuator 27 such that the screw 14 penetrates into the pole 11 over a predetermined distance D1 as represented in FIG. 3. The penetration of the screw 14 is made along an angle α with respect to the ground S and the screw 14 extends into the pole 11 below the level of the ground S. During movements of the screw 14 up to the predetermined distance D1, the sensor 17 measures the efforts of the screw 14. The distance D1 is preferably between 40 and 60 mm. This measurement Ev is transmitted to the circuit 24 which displays said measurement Ev on the display 32 for the operator in a step 42. Following said step 42, the screw 14 ensures that the device 10 is maintained on the pole 11.

Figure 4:
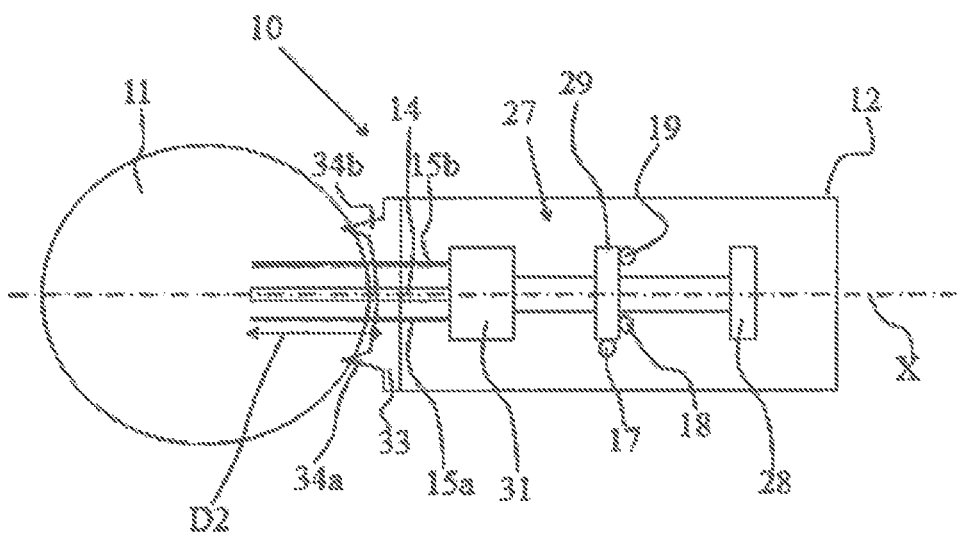

The operator then actuates the trigger 22, and in a step 43, the circuit 24 controls the coupling 31 in order to associate the movements of the actuator 27 with the two tips 15a, 15b. The circuit 24 also actuates the actuator 27 such that the tips 15a, 15b penetrate one after the other into the pole 11 over a predetermined distance D2 as represented in FIG. 4. The distance D2 is preferably between 40 and 60 mm. As a variant, the two tips 15a, 15b contemporaneously penetrate the pole 11.

The penetration of each tip 15a, 15b is performed at the angle α with respect to the ground S, and each tip 15a, 15b extends into the pole 11 beneath the level of the ground S. The angle of the screw 14 with respect to the frame 12 being identical to the angle of the tips 15a, 15b with respect to the frame 12, the force exerted on the frame 12 during the step 43 has a direction opposite to the holding force of the frame 12 by the screw 14. During the movements of the two tips 15a, 15b up to the predetermined distance D2, the sensor 19 measures the efforts of the actuator 27 for insertion of each tip 15a, 15b. These two measurements Ep are transmitted to the circuit 24 which displays said measurements Ep on the display 32 for the operator in a step 44.

Once again the operator actuates the trigger 22 when he has noted the measurements Ep, and in a step 45, the circuit 24 queries the sensor 18 for the measurement of an electrical resistivity Re between the ends of the two tips 15a, 15b that are inserted into the pole 11. Said measurement Re is transmitted to the circuit 24 which displays said measurement Re on the display 32 for the operator in a step 46.

The measurements being completed, the operator actuates the trigger 22 in such a way that in a step 47, the circuit 24 actuates the actuator 27 in order to withdraw the tips 15a, 15b from the pole 11. When the tips 15a, 15b have retracted to their initial positions, the circuit 24 informs the operator on the display 32 in a step 48. The operator actuates the trigger 22 one last time in such a way that, in a step 49, the circuit 24 controls the coupling 31 in order to associate the movements of the actuator 27 with the Screw 14. The circuit 24 also actuates the actuator 27 such that the screw 14 is retracted to the initial position thereof. When the screw 14 has reached the initial position the, the circuit 24 so informs the operator in a step 50 by means of the display 32. Following said step 50, the screw 14 ensures that the device 10 is maintained on the pole 11. The last step 51 consists in extracting the two tips 34a, 34b from the pole 11 in order to completely remove the device 10.

Preferably, the movements of the actuator 27 are regulated by the servo valve 30 controlled by the circuit 24 during steps 41, 43 for movement of the screw 14 and/or the tips 15a, 15b within the pole 11. The tips 15a, 15b and/or the screw 14 can also be mounted on fixing elements that are removable with respect to the frame 12 in such a way as to facilitate the replacement of said tools. The screw 14, for example, can be changed by the operator as a function of the substance and the diameter of the pole 11.

The embodiment describes a display of the measurements Ev, Ep and Er directly on the display 32 for the operator. The operator can thus estimate the safety status and remaining working life of the pole 11 as a function of the measurements Ev, Ep and Er. As a variant, the circuit 24 comprises means of storing the measurements Ev, Ep and Er and processing means capable of estimating the safety status and remaining working life of the pole 11. In another variant, the circuit 24 comprises means of wireless transmission of the measurements Ev, Ep and Er, and a remote computer receives said measurements Ev, Ep and Er and performs the analysis. In addition to the measurements Ev, Ep and Er, other information can also be taken into consideration in order to estimate the safety status and remaining working life, such as the substance of the pole 11, the diameter and the type of chemical processing undergone by the pole 11.

Thus, the invention makes it possible to test the quality of a pole 11 and to estimate the safety status and remaining working life thereof. As a variant, the invention can be utilized to characterize any type of hygroscopic material such as wood or other similar construction materials.

The invention claimed is:

1. Metrology device for determining a quality of a hygroscopic material, the device comprising:
   a frame,
   a support element suitable for attaching the frame to the hygroscopic material,
   two tips translatable with respect to the frame,
   a first penetration effort sensor for measuring a penetration effort (Ep) of each of the two tips as a function of a force applied to each of the two tips to reach a predetermined distance of insertion, and
   a resistivity sensor for measuring an electrical resistivity (Re) between the two tips, wherein the resistivity sensor is adapted to measure an electrical resistivity of the hygroscopic material between the two tips when the two tips are inserted into the hygroscopic material,
   wherein the support element penetrates into the hygroscopic material to fix the frame to the hygroscopic material, and
   wherein the device further comprises:
      a second penetration effort sensor for measuring a penetration effort (Ev) of the support element as a function of a force applied to the support element to reach a predetermined fixing position.

2. Metrology device according to claim 1, wherein the device further comprises
   at least one actuator for moving at least one of the two tips and the support element, and an actuator controller.

3. Metrology device according to claim 2, wherein the device further comprises an actuator regulator.

4. Metrology device according to claim 1, wherein the device further comprises at least one independent energy source.

5. Metrology device according to claim 1, wherein the device further comprises a guide part adapted to guide a position of the frame with respect to the hygroscopic material, the guide part comprising two tips adapted to be inserted into the hygroscopic material.

6. Metrology device according to claim 1, wherein at least one of the two tips and the support element is mounted on fixing elements, wherein the fixing elements are removable with respect to the frame.

7. Metrology device according to claim 1, wherein the device further comprises:
   a storage device for storing values for the penetration effort (Ep) of each of the two tips, for the electrical resistivity (Re), and for the penetration effort (Ev) of the support element, and
   a processor adapted to estimate a safety status and remaining working life of the hygroscopic material as a function of the penetration effort (Ep) of each of the two tips, the electrical resistivity (Re), and the penetration effort (Ev) of the support element.

8. Metrology device according to claim 1, wherein the device further comprises:
   a transmitter located inside the frame adapted to transmit the penetration effort (Ep) of each of the two tips, the electrical resistivity (Re), and the penetration effort (Ev) of the support element, and
   a computer, remote with respect to the frame, the computer comprising:
      a receiver adapted to receive information from the transmitter,
      a storage device for storing parameters of the hygroscopic material, and
      a processor adapted to estimate a safety status and remaining working life of the hygroscopic material as a function of the penetration effort (Ep) of each of the two tips, the electrical resistivity (Re), the penetration effort (Ev) of the support element, and the parameters of the hygroscopic material.

9. Metrology device according to claim 8, wherein the parameters of the hygroscopic material comprise a substance of the hygroscopic material, a diameter, type of chemical processing undergone by the hygroscopic material, and an above-ground length of the hygroscopic material.

10. Metrology device according to claim 1, wherein the predetermined distance of insertion of the two tips is between 40 mm and 60 mm.

11. Metrology device according to claim 1, wherein the support element is a screw, the screw having a diameter adapted to a substance of the hygroscopic material and a diameter of the hygroscopic material.

12. Metrology device according to claim 1, wherein the hydroscopic material comprises one of a wood and a construction material.

13. Metrology device according to claim 1, wherein the hydroscopic material comprises a wooden pole.

14. Metrology method for determining a quality of a hygroscopic material, the method comprising:
   inserting two tips into the hygroscopic material a predetermined distance,
   measuring, for each of the two tips, a penetration effort (Ep) as a function of a force applied to each of the two tips to reach the predetermined distance,
   when the two tips have reached the predetermined distance, measuring an electrical resistivity (Re) between the two tips,
   estimating an internal hygrometry of the hygroscopic material as a function of the electrical resistivity (Re),
   inserting a support element into the hygroscopic material at an angle with respect to a frame, wherein the angle is substantially equal to an angle of penetration of the two tips with respect to the frame, measuring a penetration effort (Ev) applied to the support element to reach a predetermined fixing position, and estimating a safety status and remaining working life of the hygroscopic material based on the penetration effort (Ep) of each of the two tips, the electrical resistivity (Re), and the penetration effort (Ev) of the support element.

15. Metrology method according to claim 14, wherein, when the hygroscopic material is planted in ground, inserting the support element into the hygroscopic material is performed at ground level (S).

16. Metrology method according to claim 14, wherein the support element penetrates into the hygroscopic material at an angle (α) with respect to ground level (S) substantially equal to an angle of penetration of the two tips with respect to ground level (S).

17. Metrology method according to claim 16, wherein the angle (α) is between 30 degrees and 45 degrees.

18. Metrology method according to claim 16, wherein, when the hygroscopic material is planted in ground, the angle (α) is between 30 degrees and 45 degrees with respect to ground level (S) such that the support element penetrates beneath ground level.

19. Metrology method according to claim 14, wherein the hydroscopic material comprises one of a wood and a construction material.

20. Metrology method according to claim 14, wherein the hydroscopic material comprises a wooden pole.

* * * * *